(12) United States Patent
Usher, Jr. et al.

(10) Patent No.: US 7,887,548 B2
(45) Date of Patent: Feb. 15, 2011

(54) SCREW INSERTION GUIDE TUBE WITH WINDOW

(75) Inventors: John A. Usher, Jr., West Palm Beach, FL (US); Ronald I. Apfelbaum, Salt Lake City, UT (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 841 days.

(21) Appl. No.: 11/634,790

(22) Filed: Dec. 5, 2006

(65) Prior Publication Data

US 2008/0132904 A1 Jun. 5, 2008

(51) Int. Cl.
*A61B 17/90* (2006.01)
(52) U.S. Cl. .......................... 606/104; 606/96
(58) Field of Classification Search ......... 600/564–567; 606/86 A, 96–98, 104, 300, 302, 304, 330–331; 81/44, 125, 124.1–124.7, 451, 456; 285/131.3, 285/335, 394–396, 401–402
See application file for complete search history.

(56) References Cited

U.S. PATENT DOCUMENTS

| | | | | |
|---|---|---|---|---|
| 841,472 A * | 1/1907 | Vanderherchen | ............. | 81/125 |
| 1,810,704 A * | 6/1931 | Gentry | ................... | 81/456 |
| 3,575,446 A * | 4/1971 | Brantley et al. | ............... | 285/85 |
| 4,827,918 A | 5/1989 | Olerud | | |
| 4,878,915 A | 11/1989 | Brantigan | | |
| 4,946,445 A * | 8/1990 | Lynn | ....................... | 604/192 |
| 5,015,247 A | 5/1991 | Michelson | | |
| 5,112,299 A * | 5/1992 | Pascaloff | ..................... | 604/22 |
| 5,425,290 A * | 6/1995 | Fought et al. | ................. | 81/44 |
| 5,484,437 A | 1/1996 | Michelson | | |
| 5,741,287 A * | 4/1998 | Alden et al. | ................ | 606/170 |
| 5,885,300 A * | 3/1999 | Tokuhashi et al. | ........... | 606/99 |
| 5,943,922 A * | 8/1999 | Rolfe | ......................... | 81/124.2 |
| 5,951,561 A * | 9/1999 | Pepper et al. | ................. | 606/80 |
| 6,013,083 A * | 1/2000 | Bennett | ...................... | 606/104 |
| 6,200,322 B1 | 3/2001 | Branch et al. | | |
| 6,416,518 B1 * | 7/2002 | DeMayo | ....................... | 606/80 |
| 6,419,678 B1 * | 7/2002 | Asfora | ......................... | 606/96 |
| 6,436,101 B1 | 8/2002 | Hamada | | |
| 6,524,318 B1 | 2/2003 | Longhini et al. | | |
| 6,776,069 B2 * | 8/2004 | Soreo et al. | ..................... | 81/54 |
| 6,929,647 B2 * | 8/2005 | Cohen | ......................... | 606/80 |
| 7,100,948 B2 * | 9/2006 | Guest | ......................... | 285/376 |
| 7,179,261 B2 * | 2/2007 | Sicvol et al. | ............... | 606/86 A |
| 7,357,804 B2 * | 4/2008 | Binder et al. | ................. | 606/96 |
| 7,422,594 B2 * | 9/2008 | Zander | ......................... | 606/80 |
| 2003/0065333 A1 * | 4/2003 | DeMayo | ....................... | 606/92 |

* cited by examiner

*Primary Examiner*—Thomas C Barrett
*Assistant Examiner*—Larry E Waggle, Jr.
(74) *Attorney, Agent, or Firm*—RatnerPrestia (57) ABSTRACT

A surgical device suitable for use in spinal fusion of the cervical vertebrae is provided. The surgical device includes an inner tubular body and an outer tubular body. The inner and outer tubular body each has a lengthwise region and a distal portion with a discontinuous wall forming a fenestration. The fenestrations are alignable to provide a passage through the wall of the surgical device. The surgical device may provide any of several benefits, including unobstructed access to a surgical site, greater stability, and improved tactile control.

14 Claims, 12 Drawing Sheets

SCREW INSERTION GUIDE TUBE WITH WINDOW

FIELD OF INVENTION

The present invention relates to surgical devices, and more specifically, an implant device for orthopedic surgery.

BACKGROUND OF THE INVENTION

Spinal surgeries to correct causes of back pain and injury have steadily increased over the past several years. Arthrodesis of the vertebrae, otherwise known as spinal fusion, has become a recognized surgical procedure for spine surgeons to treat fractured vertebrae, disc herniations, deformities, and other spinal problems. Spinal fusion surgery typically includes immobilizing one or more vertebrae by plates, screws, cages, or other implantable fixation devices. Depending on the type of surgery and location of vertebrae fusion, entry point incisions can be made from the posterior (back) or anterior (front) of the patient along the cervical (neck), thoracic (chest), or lumbar (lower back) regions.

In the case of posterior spinal surgery, spinal fusion operation is complicated by the fact that major blood vessels lie to either side of the operative area. In addition, the spinal cord, nerves, and other tissues encased or surrounding the vertebrae are particularly exposed. Extreme care and precision are required to prevent damage of vital tissues during spinal surgery and vertebrae fusion.

Spinal implant devices currently used for spinal fusion, especially in the C1 cervical spine near the base of the skull, lack the ability to remove fixing devices, such as pedicle screws, without excessive side to side loosening. In the C1 cervical spine, where there are sensitive tissues and complex bone structure, when an inserted instrument becomes jammed, lateral movement or force will tend to damage the surrounding area. In addition, screws that are threaded into a vertebrae at an angle with respect to an opening may damage sensitive tissues such as arteries and nerves in the back of the neck. The surgeon's lack of control over screw exit angle, as well as entry angle, is a problem in performing this type of cervical spinal fusion procedure. Even further, during cervical spinal surgery the surgical field is often obstructed, and complicated instruments can block a significant view of the surgical site. Although many developments have been made in the art of surgical devices for spinal surgery, further improvements are needed to reduce the visual and manual obstruction in the surgical field.

SUMMARY OF THE INVENTION

In one aspect, the invention provides a surgical device having an inner tubular body and an outer tubular body that are rotatable with respect to each other. The inner and outer tubular body each have a lengthwise region and a distal portion with a discontinuous wall. Each discontinuous wall forms a fenestration along the distal portion which extends to the distal end of each of the inner and outer tubular bodies. The fenestrations on the inner and outer tubular bodies are alignable in a first position to provide a passage through the side wall of the surgical device. When the inner and outer tubular bodies are rotated with respect to each other to a second position, the fenestrations oppose each other to form a generally tubular wall along the length of the surgical device.

In another aspect, a method for using a surgical device having an inner tubular body and an outer tubular body is provided. The method includes the step of disposing the inner tubular body and outer tubular body with respect to each other to provide a generally continuous wall along the surgical device. The inner tubular body or outer tubular body is then rotated with respect to the other to provide an opening in the side wall of the surgical device. A surgical screw can be disengaged from the surgical device through the opening in the side wall by sliding the surgical device sideways.

BRIEF DESCRIPTION OF THE DRAWINGS

The features of the invention and the elements characteristic of the invention are set forth with particularity in the appended claims. The figures are for illustration purposes only and are not necessarily drawn to scale. The invention itself, however, may best be understood by reference to the detailed description which follows when taken in conjunction with the accompanying drawing in which:

DETAILED DESCRIPTION OF THE INVENTION

The invention will next be illustrated with reference to the figures. Such figures are intended to be illustrative rather than limiting and are included herewith to facilitate the explanation of the present invention. The figures are not necessarily to scale, and are not intended to serve as engineering drawings.

Figure 1:
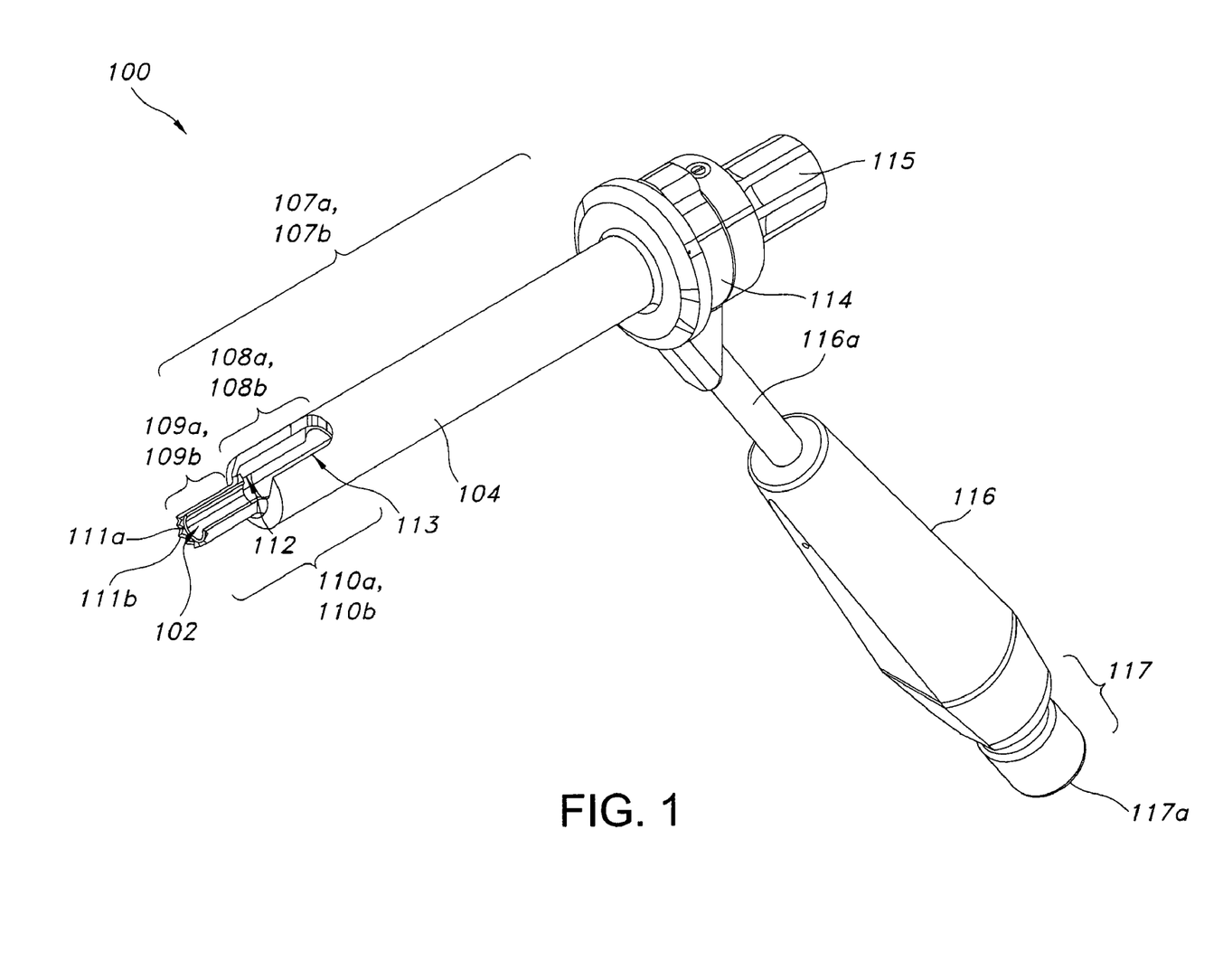
FIG. 1 is a perspective view of an exemplary embodiment of a surgical device in accordance with the present invention.

Referring generally to the drawings (FIGS. 1-11), the invention provides a surgical device 100 having an inner tubular body 102, an outer tubular body 104, and a handle 116. The inner tubular body 102 has a lengthwise region 107a and a distal portion 110a with a discontinuous wall. The discontinuous wall on the inner tubular body 102 forms a fenestration 112 along the distal portion 110a which extends to the distal end 111a of the inner tubular body 102. The outer tubular body 104, similarly, has a lengthwise region 107b and a distal portion 110b with a discontinuous wall. The discontinuous wall on the outer tubular body 104 forms a fenestration 113 along the distal portion 110b which extends to the distal end 111b of the outer tubular body 104. The inner tubular body fenestration 112 and the outer tubular body fenestration 113 are alignable in a first position to provide a passage through the wall of the assembled surgical device 100 (as shown in FIG. 1). When the inner tubular body 102 and outer tubular body 104 are rotated with respect to each other to a second position, the fenestrations 112, 113 oppose each other to form a generally tubular wall along the length of the surgical device 100 (as shown in FIG. 4).

As noted above, FIG. 1 depicts an exemplary embodiment of the surgical device of the present invention. The surgical device 100 includes an inner tubular body 102 and an outer tubular body 104 that are rotatable with respect to each other. The inner tubular body 102 is able to be inserted and removed from the outer tubular body 104 such that when the inner tubular body 102 is inserted or removed from the outer tubular body 104, the outer surface of the inner tubular body 102 generally slidingly contacts the inner surface of the outer tubular body 104.

In the first position, the fenestrations 112, 113 generally provide an open window configuration in which the distal region of the inner surface of the inner tubular body 102 is exposed. When the inner tubular body 102 and the outer tubular body 104 are rotated with respect to each other to a second position (180° in the embodiment shown), the fenestrations 112, 113 oppose each other to form a generally tubular wall along the length of the assembled surgical device 100. Thus, in the second position, the fenestrations 112, 113 provide a closed window configuration in which an outer surface portion of the distal region of the inner tubular body 102 is exposed through the fenestration 113 in the outer tubular body 104, as shown for example in FIG. 4.

As shown in FIG. 1, in a preferred embodiment, the distal portion 110a of the inner tubular body 102 and the distal portion 110b of the outer tubular body 104 are defined by a respective proximal region 108a, 108b and end region 109a, 109b. In this embodiment, each of the end region 109a of the inner tubular body 102 and the end region 109b of the outer tubular body 104 has a smaller diameter than its respective proximal region 108a, 108b. In other embodiments, however, it is contemplated that the diameters could be the same.

The distal end 111b of the outer tubular body 104 may have grooves, jagged edges, or other securing means to securely position the device to a surgical site in a human or animal.

When the inner tubular body 102 or outer tubular body 104 is rotated with respect to the other to align in a first position, the inner tubular body fenestration 112 aligns with the outer tubular body fenestration 113 such that the inner surface of the inner tubular body 102 at the proximal region 108a and end region 109a is exposed. When the inner tubular body 102 or outer tubular body 104 is rotated with respect to the other to a second position (e.g. 180° in the embodiment shown in FIG. 4), the inner tubular body fenestration 112 is covered by the distal portion 110b wall, such that a continuous wall is formed along the surgical device 100. In other words, an outer surface portion of the inner tubular body 102 is exposed through the outer tubular body fenestration 113 along the proximal region 108b and end region 109b.

In various embodiments, the inner tubular body 102 may be rotated with respect to the outer tubular body 104 via inner tubular body handle 115. Furthermore, the outer tubular body 104 can be rotated with respect to the inner tubular body 102 via handle 116 or via any surface portion on outer tubular body 104 itself.

As seen in FIG. 1, a collar 114 is disposed around an outer surface portion of the outer tubular body 104. The collar has a handle 116 attached thereto. Both the collar 114 and attached handle 116 are rotatable around the outer tubular body 114 to enable an optimum holding angle and prevent visual obstruction of a surgical area. The handle 116 includes a locking mechanism 117 to lock the handle 116 and collar 114 and thereby prevent them from rotating with respect to outer tubular body 104. Locking mechanism 117 may include an adjustable knob 117a and at least one rotatable shaft that is disposed within the outer shaft 116a. The knob 117a may be rotated in a clockwise direction to extend at least one projection toward the outer tubular body 104. This allows the projection to contact the outer surface of outer tubular body 104 and frictionally engage it, and thereby prevent the handle 116 and collar 114 from rotating around the outer tubular body 104. The adjustable knob 117a may be rotated in a counter-clockwise direction to retract the projection and allow the collar 114 and handle 116 to freely rotate about the tubular body. It is noted that the direction in which the adjustable knob 117a is rotated is arbitrary as long as one direction locks the handle and another direction unlocks the handle.

It is further contemplated that any component of the surgical device 100 including the collar 114, handle 116, inner tubular body 102, and outer tubular body 104 can by made from any suitable material such as titanium, stainless steel, other metal alloys, and polymeric materials with a high stiffness modulus and strength.

Figure 2:
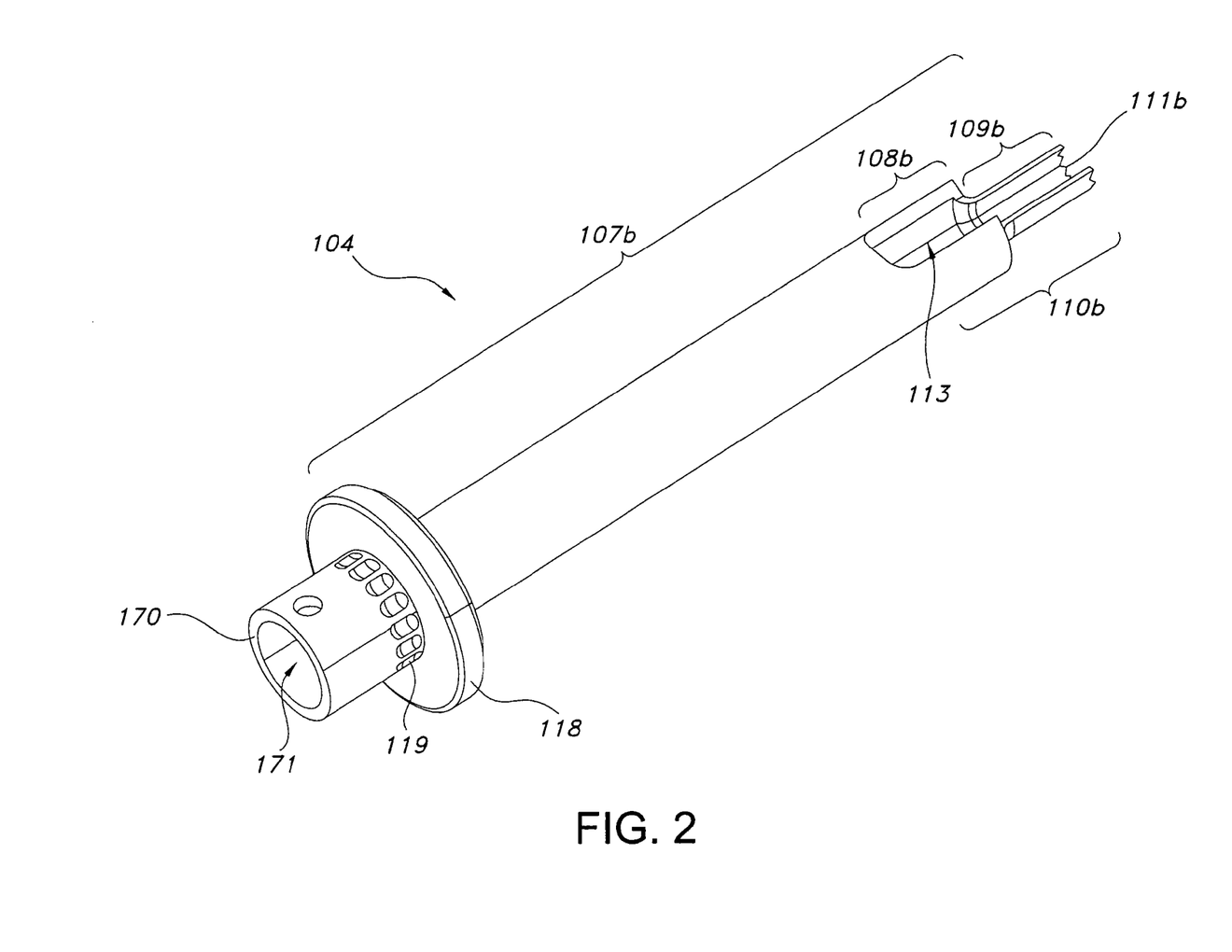
FIG. 2 is a perspective view of a component of the surgical device to show the top features with parts normally not visible.

FIG. 2 depicts an embodiment of the outer tubular body 104 component of the present invention as shown in FIG. 1. Outer tubular body 104, as illustrated in FIG. 2, has a lengthwise region 107b and a distal portion 110b with a discontinuous wall that forms a fenestration 113. The fenestration 113 is formed along distal portion 110b which extends to the distal end 111b of outer tubular body 104. Distal portion 110b in this embodiment is defined by a proximal region 108b and an end region 109b having a smaller diameter than the proximal region 108b. The transition between the two regions of different diameters can be either gradual (tapered) or instant.

The distal end 111b of the outer tubular body 104 may have grooves, jagged edges, or any other means to help secure the device to a surgical site.

Proximal end 170 opposite distal end 111b defines an opening 171 to receive inner tubular body 102. When inner tubular body 102 is inserted into outer tubular body 104, the inner surface of the outer tubular body 104 preferably slidingly engages the outer surface of the inner tubular body 102.

A rim portion, or flange 118, projects from the side wall of the outer tubular body 104 in the embodiment shown in FIG. 2 and provides a surface against which a collar can be positioned. Notches 119 are adjacent to the flange 118 in this embodiment and provide engagement surfaces to matingly interact with, and receive the, locking mechanism projection in the handle has discussed above.

Figure 3:
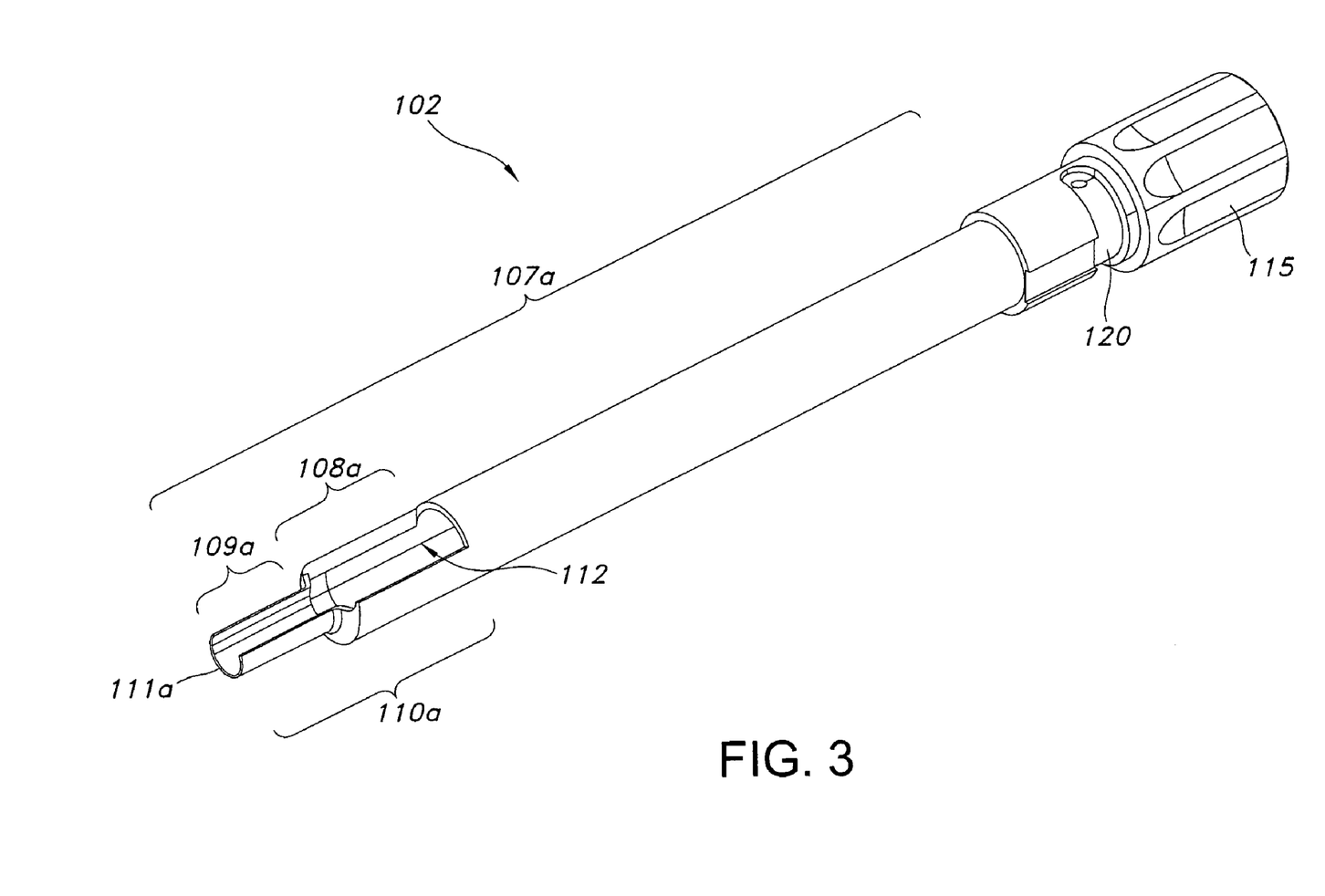
FIG. 3 is a perspective view of a component of the surgical device.
Figure 4:
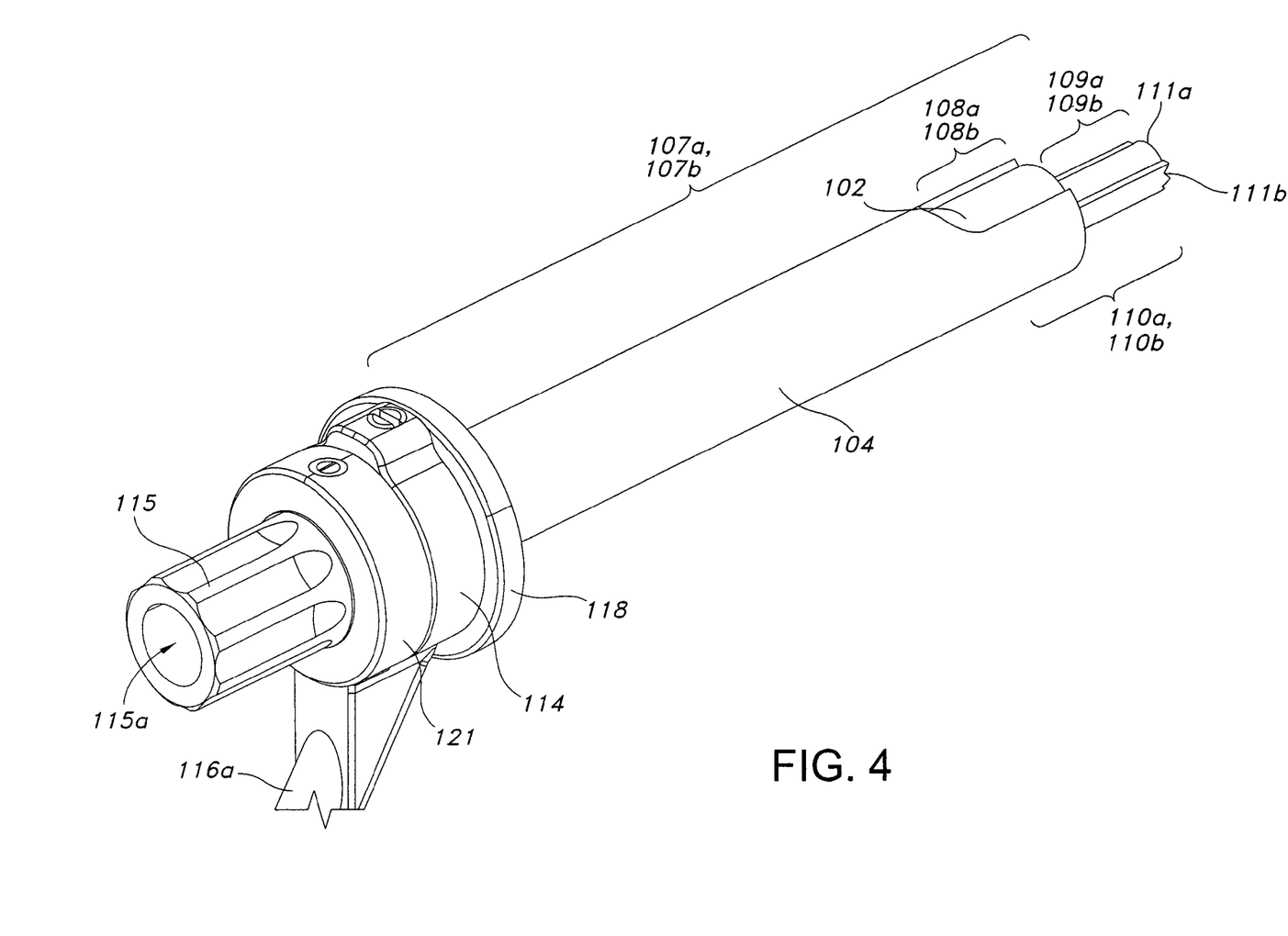
FIG. 4 is a larger perspective view of an embodiment of the present invention.

FIG. 3 depicts an embodiment of an inner tubular body 102 component of the present invention. As described above, inner tubular body 102 includes a lengthwise region 107a with a distal portion 110a having a discontinuous wall forming fenestration 112. In the embodiment shown, the inner tubular body 102 includes handle 115 for rotating the inner tubular body 102 with respect to the outer tubular body 104, and circumferential recess 120 that extends 180° around the outer surface circumference of the inner tubular body 102. The inner tubular body 102 is inserted into outer tubular body 104 generally near the midpoint of recess 120 (e.g. 90°), such that recess 120 receives a male protrusion extending perpendicularly and radially inward from the inner surface of the outer tubular body 104. When the inner tubular body 102 or outer tubular 104 is rotated with respect to the other, away from the midpoint of recess 120, the male protrusion contacting recess 120 prevents removal of the inner tubular body 102 from the outer tubular body 104. Therefore, when the inner tubular body 102 is rotated with respect to outer tubular body 104 90° from the midpoint of recess 120 to a first position, a passage is provided through the wall of the surgical device (e.g. an open window configuration), and the inner tubular body 102 is prevented from being removed from the outer tubular body 104. When the inner tubular body 102 is rotated with respect to the outer tubular body 104 180° from the first position to a second position, a generally tubular wall is formed along the device (e.g. a closed window configuration), and the inner tubular body 102 is also prevented from being removed from the outer tubular body 104. By preventing the inner tubular body 102 from being removed from the outer tubular body 104 in both the open and closed window positions, additional tactile control is provided to prevent error during surgery.

FIG. 4 depicts an enlarged perspective view of an exemplary embodiment of the present invention. As described above, when inner tubular body 102 is inserted into outer tubular body 104, the inner tubular body 102 can be prevented from being removed from the outer tubular body 104 by rotating the inner tubular body 102 or outer tubular body 104 away from the midpoint of recess 120 (FIG. 3). The surgical device 100 as shown has the inner tubular body fenestration 112 (FIG. 3) and outer tubular body fenestration 113 (FIG. 2) opposing each other in a second position. This provides a closed window configuration that forms a generally tubular wall along the length of the device. When the inner tubular body 102 or outer tubular body 104 is rotated 180° with respect to the other from the second position to the first position, the fenestrations 112, 113 align to provide an opening in the side wall of the surgical device 100 (FIG. 1).

As further seen in FIG. 4, a handle portion 115 on the inner tubular body 102 extends away from the outer tubular body 104 and has an opening 115a to receive surgical screws or interchangeable instruments such as an awl, a drill, or a tap. The surgical screws and interchangeable instruments are described in detail below.

FIG. 4 also shows ring 121 secured around the outer tubular body 104. Ring 121 is adjacent to collar 114 to prevent the collar 114 and handle 115 from being removed from the device.

When the surgical device 100 is in use at a surgical site, the inner tubular body 102 or outer tubular body 104 is rotated to with respect to the other to form the generally tubular wall along the length of the device 100. Interchangeable instruments may be inserted/removed through opening 115a and operated individually to gain further access to the surgical site. For example, an instrument may be used with the surgical device 100 to puncture a hole in a vertebrae and another instrument may be used to drill a shaft in the bone. After the instruments have been used, a surgical screw is inserted through opening 115b and is confined by the inner tubular body 102 wall. When the screw has been threaded into the vertebrae, the inner tubular body 102 is rotated via handle 115 to provide an opening in the side wall of the surgical device 100. A surgeon may operably slide the device 100 sideways to release the surgical screw through the inner tubular body fenestration 112 and the outer tubular body fenestration 113. This configuration provides the benefit of additional stability and precise threading angle with the use of the narrow end region 109a, 109b.

Figure 5:
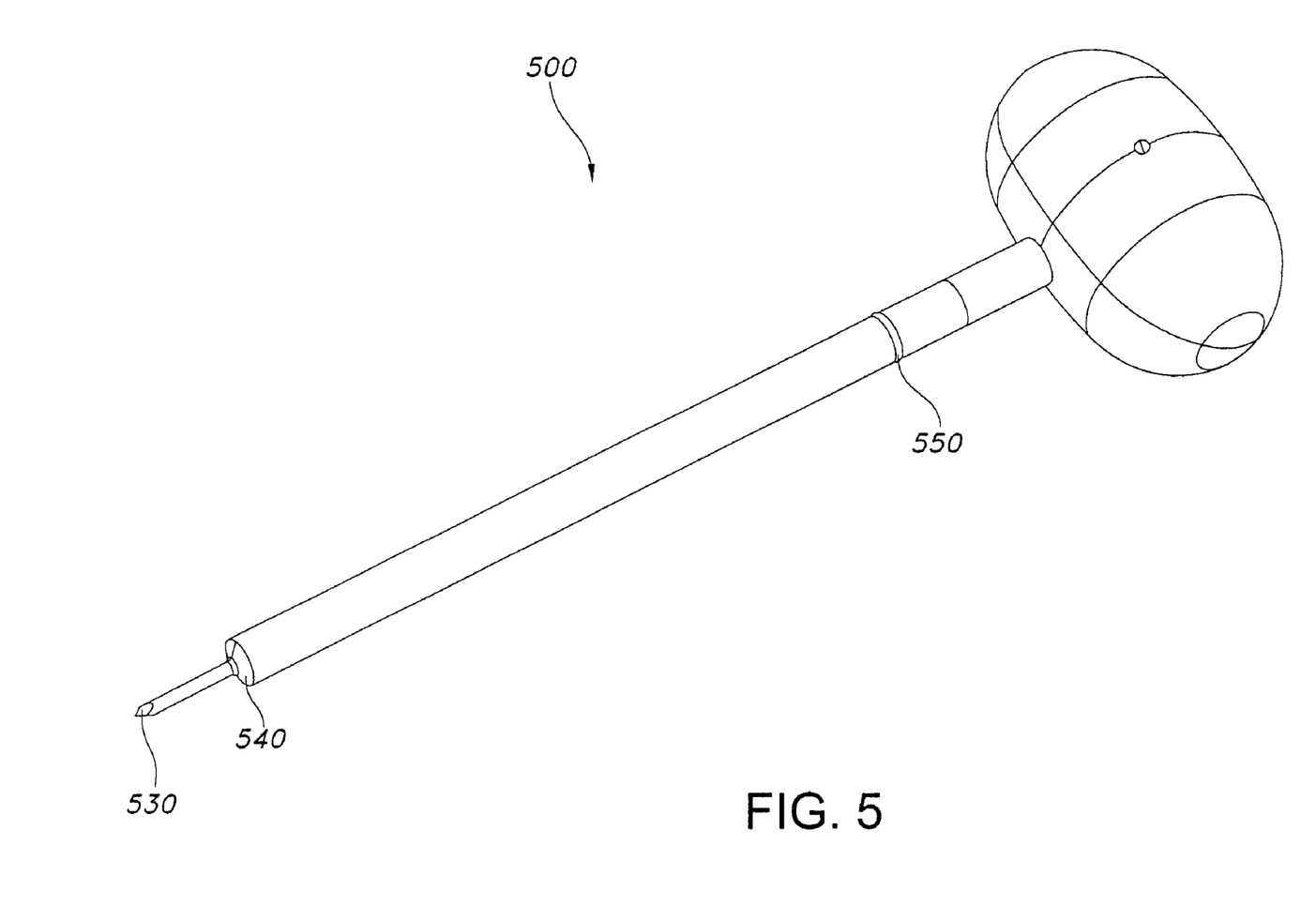
FIG. 5 is a perspective view of an attachment for an embodiment of present invention.

FIG. 5 depicts an embodiment of an interchangeable device to be used with the surgical device. The interchangeable device shown is awl 500 which can be inserted into the inner tubular body. In a preferred used, awl 500 is used to puncture the cortex of the vertebrae and includes a pointed distal tip 530, a positive stop 540, and an indicator groove 550. When the awl is inserted within the inner tubular body, the positive stop 540 is positioned within and against the proximal region 108a (FIGS. 1-4) and the pointed distal tip 530 extends through and beyond the end region 109a (FIGS. 1-4). For the C1 cervical vertebrae, the positive stop 540 on the awl prevents an insertion depth greater than 4 mm, but it is contemplated that the insertion depth may be greater than 4 mm for other vertebrae such as those in the thoracic and lumbar regions. An indicator groove 550 provides an indication of the positive stop position when used with the surgical device described herein.

Figure 6:
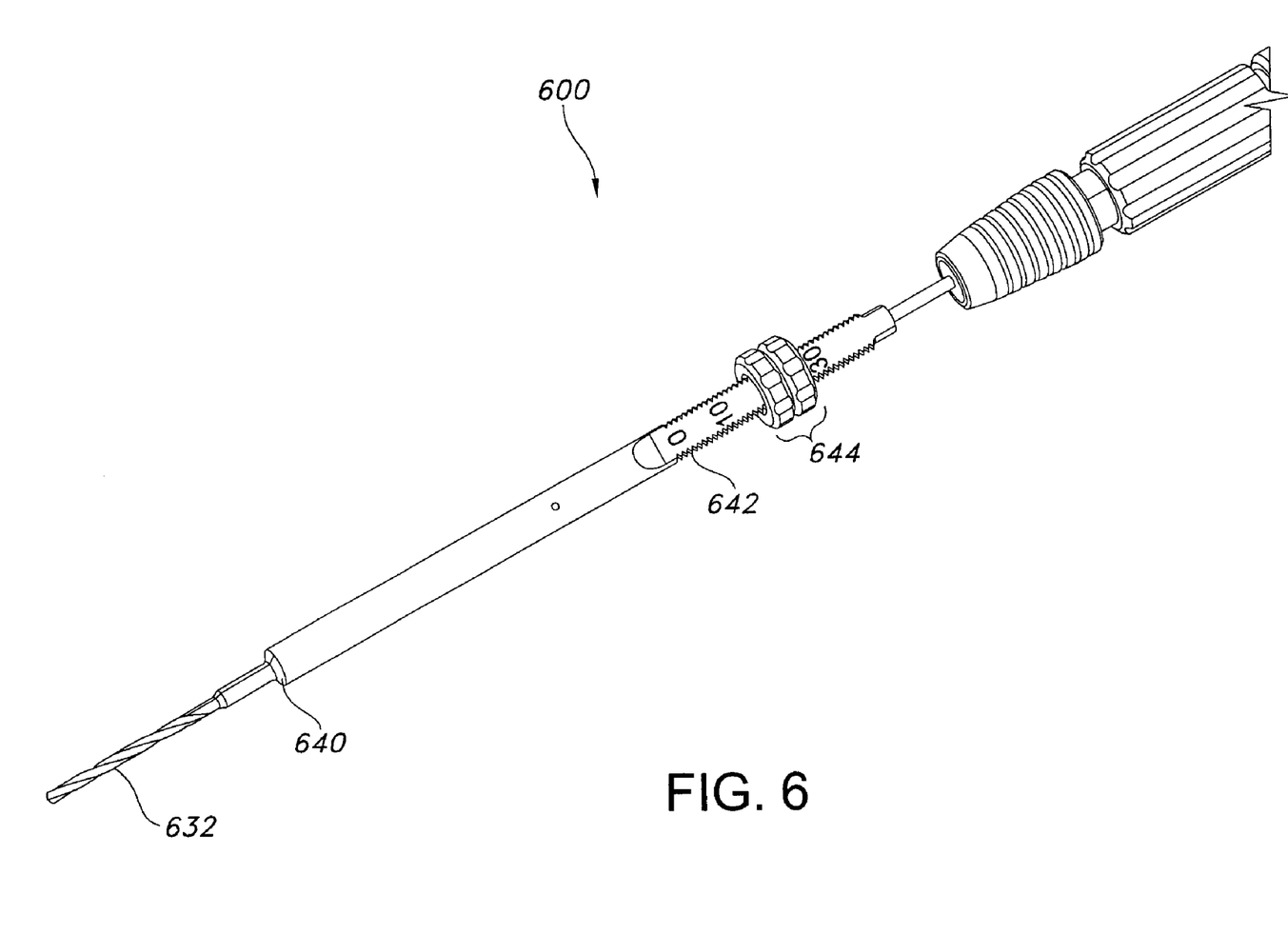
FIG. 6 is a perspective view of a second attachment for an embodiment of present invention.

FIG. 6 depicts an embodiment of a second interchangeable device useable with the surgical device described herein. The interchangeable device shown is drill 600 which is inserted into the inner tubular body. The drill is used to drill an in-line shaft along the puncture in the vertebrae previously made by the awl. The drill includes a drill bit 632, a positive stop 640, a thread shaft 642, and an adjustable locking system 644. The drill bit drills into the vertebrae cortex and has a diameter for 4 mm surgical screws. It is contemplated that in other embodiments, the drill bit may have any suitable diameter for various sized surgical screws. Positive stop 640 prevents a drill insertion depth generally greater than 40 mm, but can be more or less than 40 mm in other embodiments. The threaded shaft 642 has a 1 mm threaded pitch to allow precise positioning of the adjustable locking mechanism 644 to a maximum drill depth of 30 mm. As noted above, the drill depth may be more or less than 30 mm, depending upon the particular vertebrae for which spinal fusion is being performed. The adjustable locking system typically includes double nut locks that are threaded in opposing directions.

Figure 7:
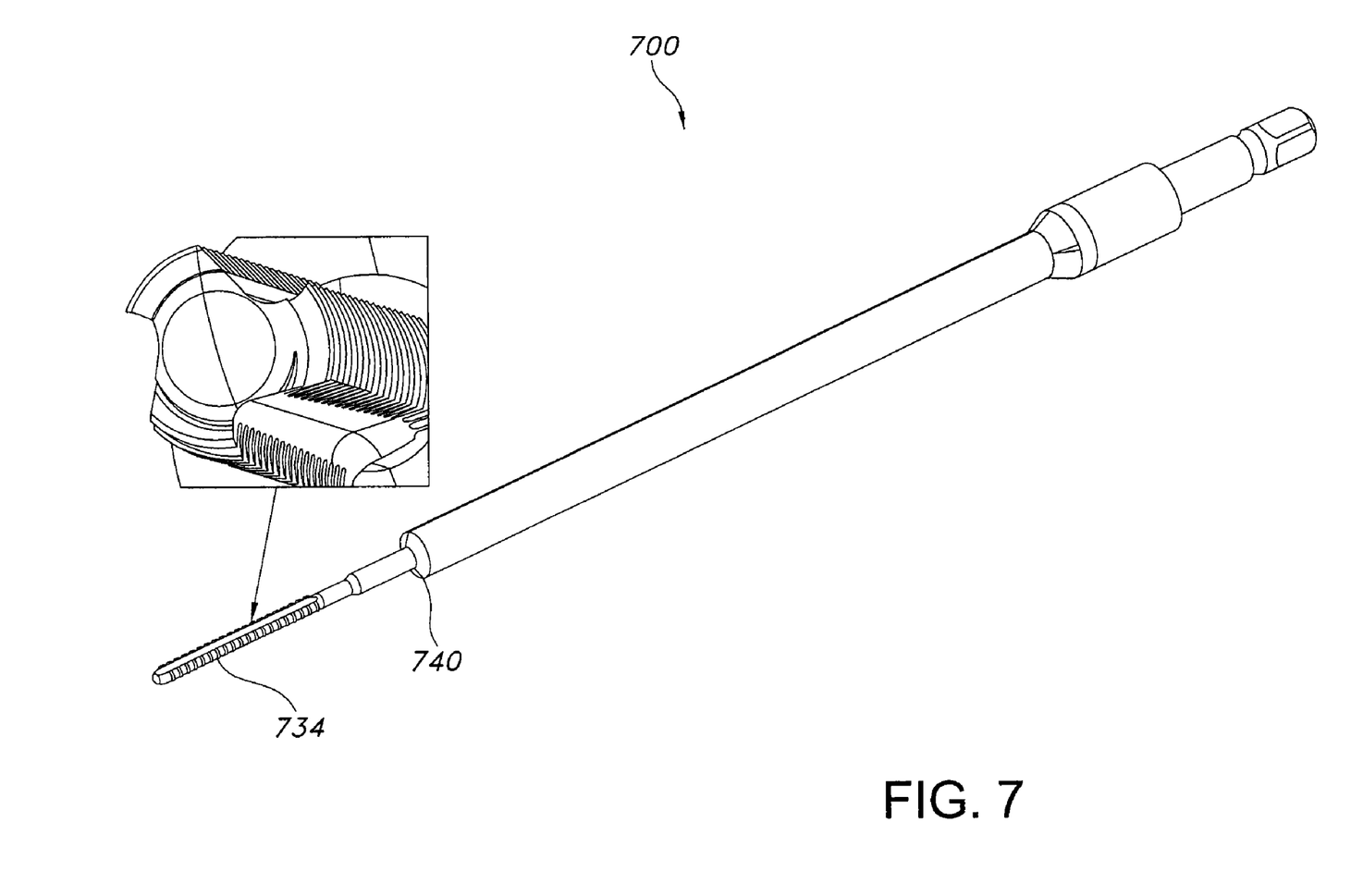
FIG. 7 is a perspective view of a third attachment for an embodiment of present invention.

FIG. 7 depicts an embodiment of a third interchangeable device useable with the surgical device. The interchangeable device shown is a tap 700 which is inserted into the inner tubular body. The tap is used to thread a drilled opening to allow a screw to be threaded into a surgical site. The tap cuts the thread for 4 mm smooth shank screws, but it is contemplated that the tap may be used to cut threads for various sized surgical screws. The tap has a threading tip 734 and a positive stop 740. The shaft is marked with a maximum tap insertion depth of 30 mm, but can be more or less than 30 mm in other embodiments.

Figure 8A:
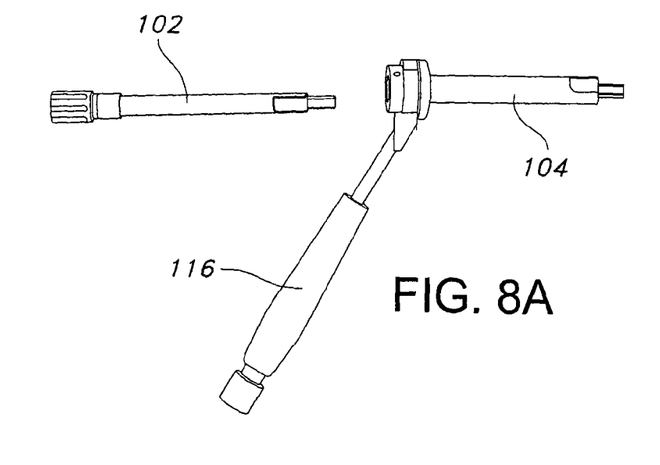
FIG. 8A is a side view of the device with a component detached.
Figure 8B:
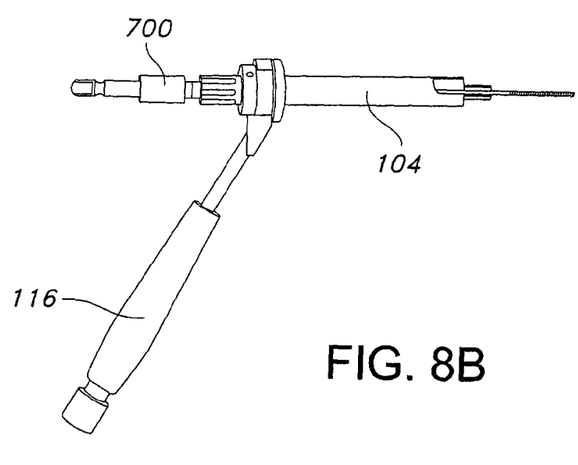
FIG. 8B is a side view of the device in use with one attachment.
Figure 8C:
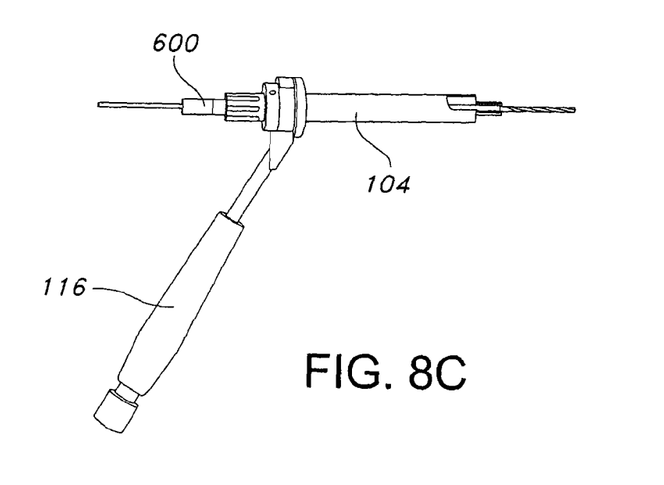
FIG. 8C is a side view of the device in use with a second attachment.
Figure 8D:
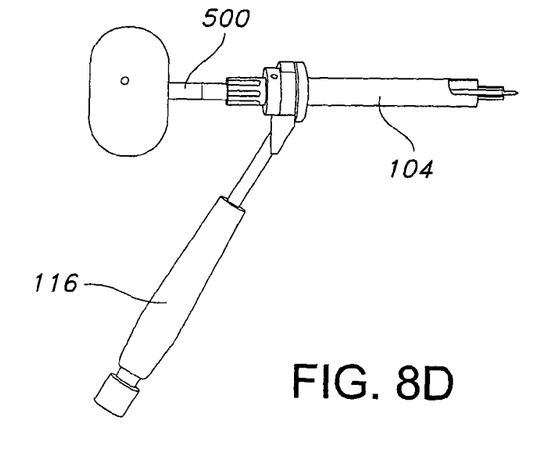
FIG. 8D is a side view of the device in use with a third attachment.

FIGS. 8A, 8B, 8C, and 8D show various exemplary embodiments of the present invention. In FIG. 8A, the inner tubular body is removed from the inner tubular body. In FIG. 8B, the inner tubular body is inserted into the outer tubular body and an tap is inserted into the inner tubular body. In FIG. 8C shows a tap removed from the inner tubular body and a drill inserted. In FIG. 8D, the drill is removed and an awl is inserted into the inner tubular body inner tubular body.

Figure 9A:
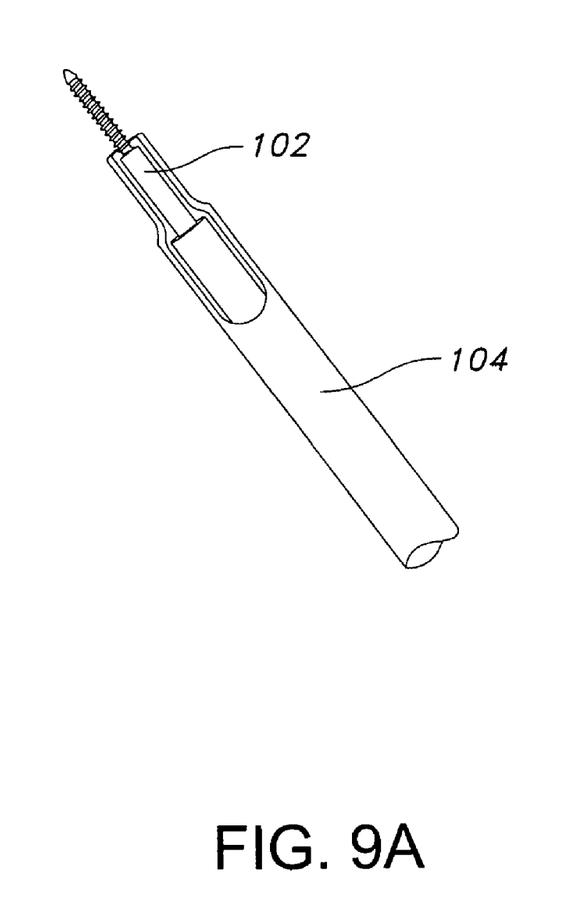
FIGS. 9A and 9B are side views of the device in use with a surgical screw.
Figure 9B:
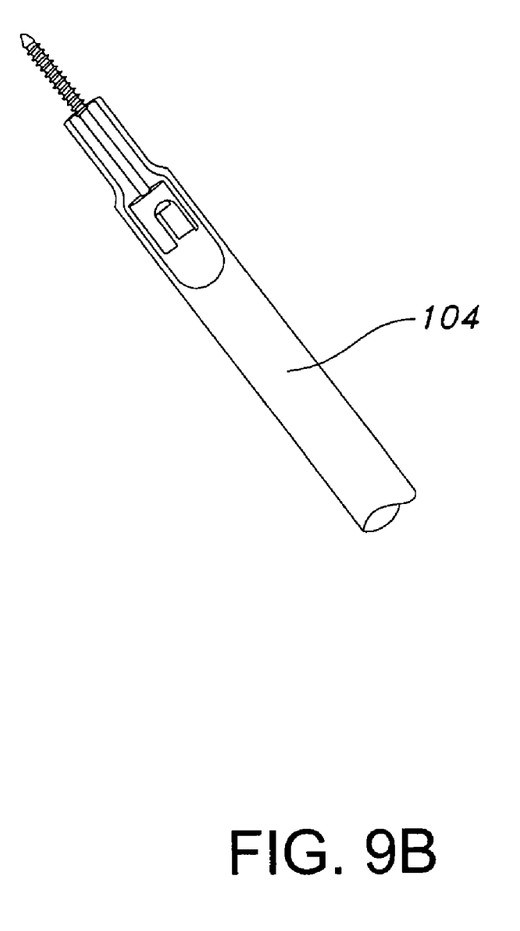

FIGS. 9A and 9B show side views of the device in use with a surgical screw. In FIG. 9A, a side view of the surgical device is depicted when the fenestrations on the inner and outer tubular body are rotated such that they oppose each other. In this closed window configuration, a generally continuous tubular wall is formed along the length of the device, such that the surgical screw is contained with the inner tubular body. FIG. 9B shows a surgical device with the fenestrations aligned with each other such that an opening is formed in the side wall of the device for access to a surgical site in a human or animal. When the surgical screw is threaded in a vertebrae, the screw can be released from the opening in the side wall by sliding the device 100 sideways. As seen in the figure, the surgical screw includes a threaded shaft and a screw head. The threaded shaft extends through the end region of the tubular bodies and the screw head is positioned in the proximal region.

Figure 10:
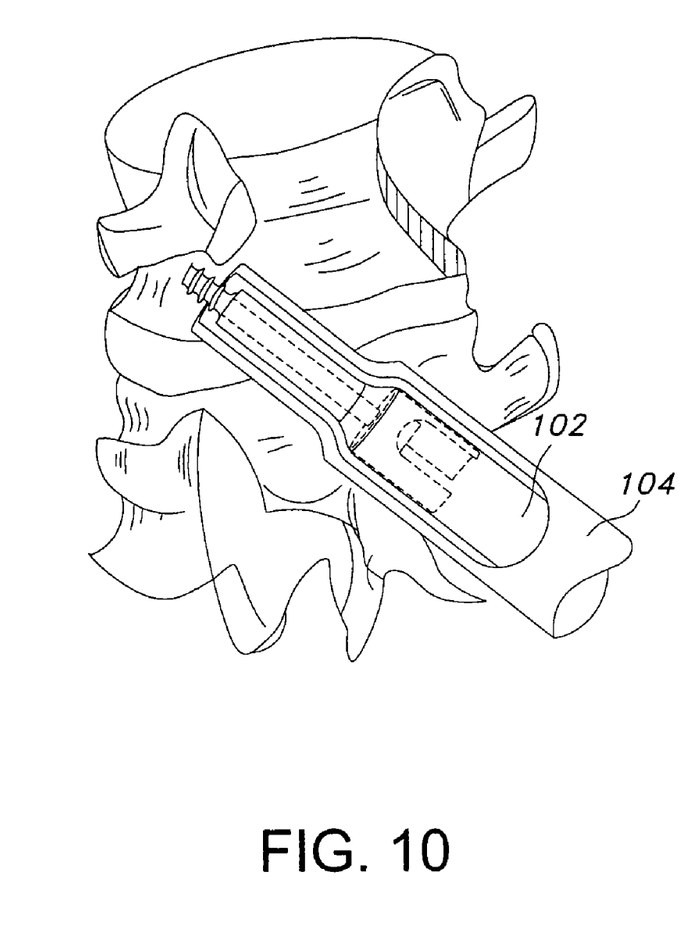
FIG. 10 is a perspective view of a surgical screw being threaded into a vertebrae.

FIG. 10 depicts a vertebrae with surgical device 100 and a surgical screw inside. The inner tubular body 102 is rotated to cover the opening in the side wall of the device 100 to allow for greater stability in threading the screw into the vertebrae.

Figure 11:
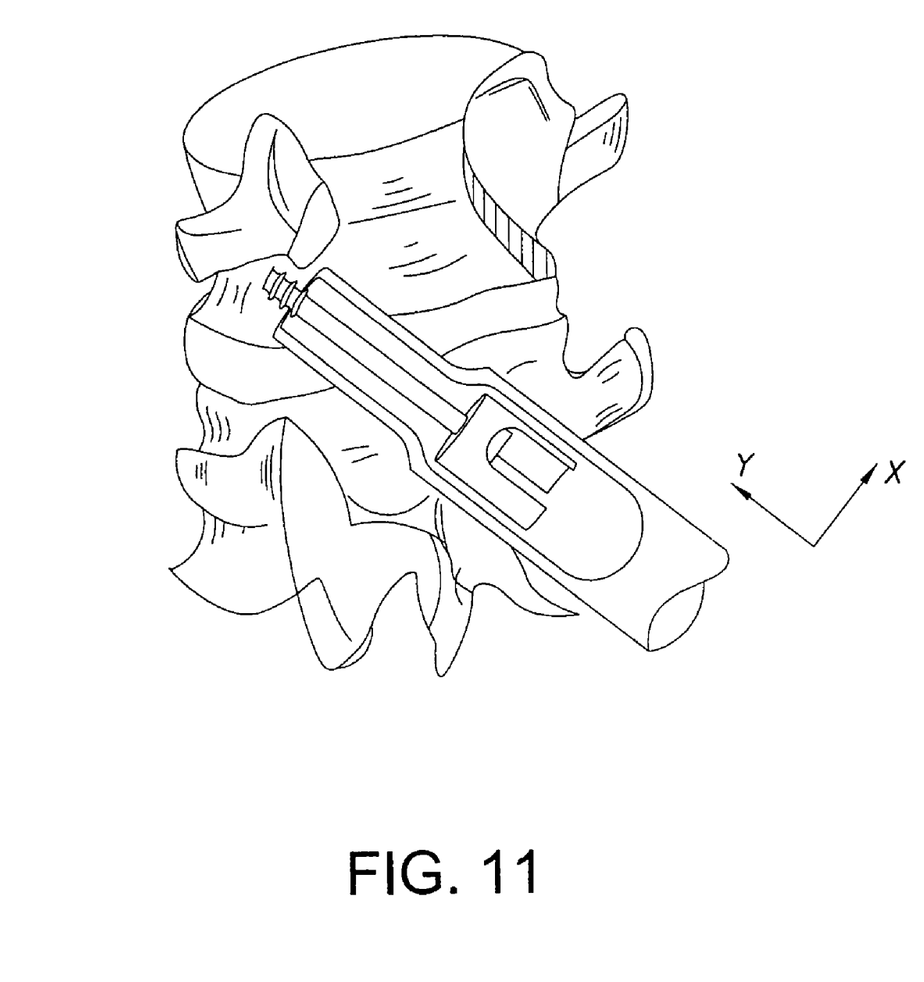
FIG. 11 is a perspective view of a surgical screw threaded into a vertebrae and the device about to be removed from the surgical site.
Figure 12:
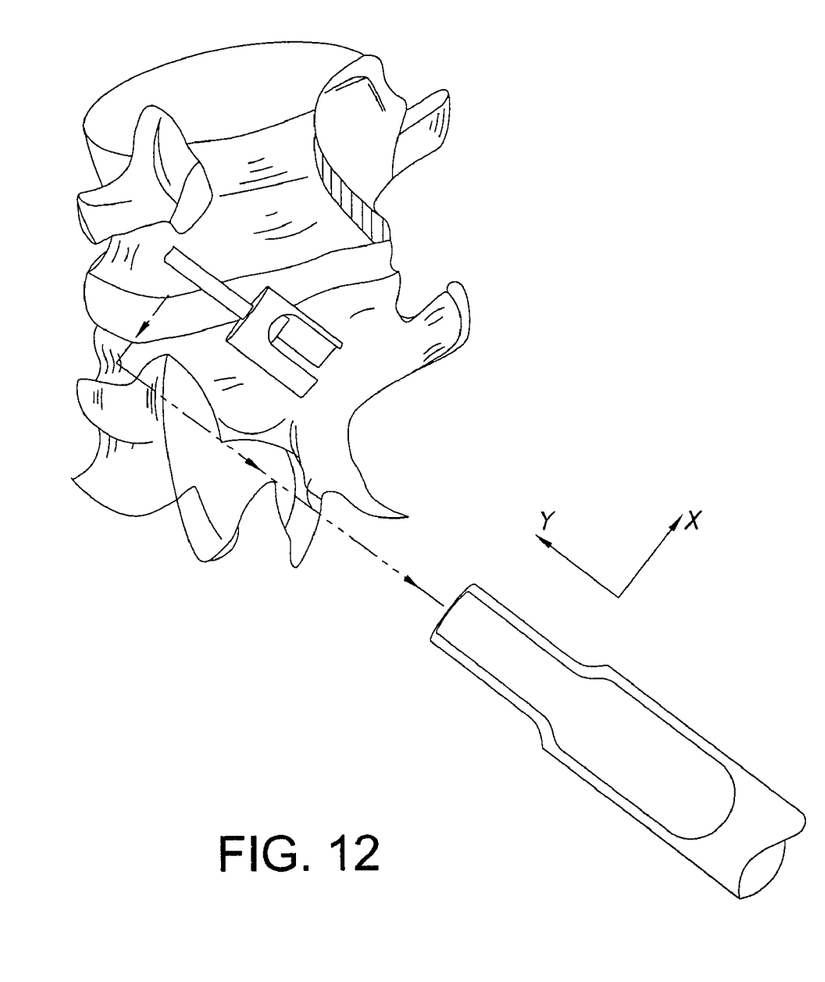
FIG. 12 is a perspective view of the surgical screw and device of FIG. 11.

FIG. 11 depicts a surgical screw threaded into the vertebrae and inner tubular body 102 rotated to reveal the surgical screw. The surgical device 100 is released from the threaded screw along a sideways axis, e.g., x-axis, and the device 100 is then removed from the surgical site along the y-axis, as depicted by the dashed arrow lines in FIG. 12.

Although the present invention has been particularly described in conjunction with specific embodiments, it is evident that many alternatives, modifications, and variations will be apparent to those skilled in the art. It is therefore contemplated that the appended claims will embrace any such alternatives, modifications, and variations as falling within the true scope and spirit of the present invention.

What is claimed:

1. A surgical device comprising:
    an inner tubular body having a discontinuous wall surrounding a circular bore, the wall having a cylindrical proximal portion and a cylindrical distal portion, the wall forming a fenestration along the distal portion which extends to a distal end of the inner tubular body, the distal portion having a smaller diameter than the proximal portion;
    an outer tubular body for placement around the inner tubular body, the outer tubular body having a discontinuous wall, the wall having a cylindrical proximal portion and a cylindrical distal portion, the wall forming a fenestration along the distal portion which extends to a distal end of the outer tubular body, the distal end of the outer tubular body having grooves to secure the device to a surgical site in a human or animal, the distal portion having a smaller diameter than the proximal portion;
    the inner tubular body and the outer tubular body rotatable with respect to each other;
    the inner tubular body including a recess around an outer surface of the inner tubular body, the recess adapted to receive a male protrusion extending from an inner surface of the outer tubular body;
    the fenestrations alignable such that when the inner tubular body is in a first position with respect to the outer tubular body, the fenestrations align to provide a passage through the wall of the surgical device, and when the inner tubular body and outer tubular body are rotated with respect to each other to a second position, the fenestrations oppose each other to form a generally tubular wall along the length of the surgical device.

2. The device of claim 1 wherein the distal portions of both the inner tubular body and outer tubular body are defined by:
    a proximal region of the distal portion; and
    an end region having a smaller diameter than the proximal region.

3. The device of claim 1, wherein the outer tubular body is rotatable with respect to the inner tubular body to cover the fenestration of the inner tubular body and thereby form a continuous channel from a proximal region of the device to the distal end of the device.

4. The device of claim 1, wherein the inner tubular body is rotatable with respect to the outer tubular body to cover the fenestration of the inner tubular body and thereby form a continuous channel from a proximal region of the device to the distal end of the device.

5. The device of claim 1, wherein the outer tubular body is rotatable with respect to the inner tubular body to expose the fenestration of the inner tubular body and thereby form an opening in the side wall of the device for access to a surgical site in a human or animal.

6. The device of claim 1, wherein the inner tubular body is rotatable with respect to the outer tubular body to expose the fenestration of the inner tubular body and thereby form an opening in the side wall of the device for access to a surgical site in a human or animal.

7. The device of claim 1, further comprising a collar disposed around the outer tubular body, the collar having a handle attached thereto.

8. A surgical device comprising:
    an inner tubular body having a discontinuous wall surrounding a circular bore, the wall having a cylindrical proximal portion and a cylindrical distal portion, the wall forming a fenestration along the distal portion which extends to a distal end of the inner tubular body, the distal portion having a smaller diameter than the proximal portion;
    an outer tubular body for placement around the inner tubular body, the outer tubular body having a discontinuous wall, the wall having a cylindrical proximal portion and a cylindrical distal portion, the wall forming a fenestration along the distal portion which extends to a distal end of the outer tubular body, the distal portion having a smaller diameter than the proximal portion; and
    a collar disposed around the outer tubular body, the collar having a handle attached thereto,
    the inner tubular body and the outer tubular body rotatable with respect to each other,
    the fenestrations alignable such that when the inner tubular body is in a first position with respect to the outer tubular body, the fenestrations align to provide a passage through the wall of the surgical device, and when the inner tubular body and outer tubular body are rotated with respect to each other to a second position, the fenestrations oppose each other to form a generally tubular wall along the length of the surgical device, wherein the collar is rotatable with respect to the outer tubular body to position the device for access to a surgical site in a human or animal.

9. The device of claim 8, wherein the handle includes a locking mechanism to lock the handle and collar from rotating with respect to the outer tubular body.

10. The device of claim 1, wherein the recess extends 180° around the outer surface of the inner tubular body.

11. The device of claim 10, wherein the inner tubular body may be inserted or removed from the outer tubular body when the recess is positioned 90° from the male protrusion.

12. The device of claim 1 wherein the inner tubular body is positioned around an interchangeable attachment selected from the group consisting of an awl, a drill, and a tap.

13. The device of claim 1 wherein the inner tubular body is positioned around a surgical screw having a lengthwise threaded shaft and a screw head, the shaft being positioned in an end region of the device and the screw head positioned in a proximal region of the distal portion.

14. The surgical device of claim 1, wherein
    the fenestration of the inner tubular body adjoins a distal opening of the inner tubular body, and
    the fenestration of the outer tubular body adjoins a distal opening of the outer tubular body.

* * * * *